(12) United States Patent
Bussell et al.

(10) Patent No.: US 6,585,942 B1
(45) Date of Patent: Jul. 1, 2003

(54) STERILIZATION CONTAINER (75) Inventors: Thomas J. Bussell, Warsaw, IN (US); Gregg Fedorka, Rosalle, NJ (US)

(73) Assignee: Paragon Medical, Inc., Pierceton, IN (US)

( * ) Notice: Subject to any disclaimer, the term of this patent is extended or adjusted under 35 U.S.C. 154(b) by 0 days.

(21) Appl. No.: 09/491,421

(22) Filed: Jan. 26, 2000

Related U.S. Application Data
(60) Provisional application No. 60/117,265, filed on Jan. 26, 1999.

(51) Int. Cl.[7] ................................................ A61L 2/20
(52) U.S. Cl. ...................... 422/300; 206/349; 206/363; 206/364; 206/365; 206/368; 220/913; 220/916; 422/297
(58) Field of Search ................................ 422/297, 300, 422/30; 206/363, 364, 365, 366, 367, 368, 369, 370, 349; 220/297, 300, 510, 578, 580, 913, 916

(56) References Cited

U.S. PATENT DOCUMENTS

| | | | |
|---|---|---|---|
| 4,190,172 A | * 2/1980 | Box | 220/510 |
| 4,915,913 A | 4/1990 | Williams et al. | 422/119 |
| 5,407,648 A | 4/1995 | Allen et al. | 422/297 |
| 5,441,707 A | 8/1995 | Lewis et al. | 422/300 |
| 5,482,067 A | * 1/1996 | Wittrock et al. | 206/363 |
| 5,524,755 A | 6/1996 | Deeds | 206/370 |
| 5,641,065 A | 6/1997 | Owens et al. | 206/370 |
| 6,012,577 A | 1/2000 | Lewis et al. | 206/370 |

* cited by examiner

Primary Examiner—Robert J. Warden, Sr.
Assistant Examiner—Sean E. Conley
(74) Attorney, Agent, or Firm—Baker & Daniels (57) ABSTRACT

A sterilization container for sterilizing, storing and transporting medical instruments is provided with a collar-shaped base, a lid, and a removable bottom received within the base. Circumferentially spaced channels are provided on the walls of the base which receive removable inserts which not only secure the bottom against upward movement relative to the base but also provide landings to support insert trays received within the container. The inserts can also be provided with slots that support dividers within the container.

20 Claims, 12 Drawing Sheets

Fig 11

STERILIZATION CONTAINER

CROSS REFERENCE TO RELATED APPLICATION

This Regular Non-Provisional Application claims priority from Provisional Application Serial No. 60/117,265 filed Jan. 26, 1999.

SUMMARY OF THE INVENTION

This invention relates to a sterilization container for sterilizing, storing and transporting medical instruments.

Medical instruments must be sterilized before use in surgery and after sterilization, a sterile environment must be maintained. Accordingly, sterilization containers are used for such purposes. These sterilization containers generally are an elongated container having walls and a bottom defining a volume in which the medical instruments are placed. This volume is closed by a removable lid. It is also necessary to position medical instruments within the container so that they are readily available to the surgeon. Accordingly, multiple internal configurations of sterilization containers are necessary, and since evolving medical technology continually provides new instruments and new procedures for performing surgery, it is desirable that sterilization containers be easily reconfigured. This is difficult with prior art sterilization containers.

The present invention provides a sterilization container that can be easily reconfigured to accommodate different medical instrument sets. According to the present invention, a sterilization container includes a base which defines a volume in which the medical instruments are placed. The base is ringed shaped, and is made of plastic. The base receives a metal bottom which is supported on a ledge circumscribing the lower edge of the base. Channels are spaced circumferentially around the inner surface of the base, and receive inserts made out of a flexible silicon rubber which are locked within ill the channels to hold the bottom in place. The inserts include outwardly projecting portions which project outwardly from the channels into the volume defined by the base. The projecting portions may be trimmed at varying heights to provide landings which support insert trays which are received within the volume defined by the base. The upper surfaces of the channels also define landings for supporting insert trays.

Accordingly, insert trays may be supported at varying heights, and multiple insert trays may be used, one placed below the other. The projecting portions of the inserts may also be configured to receive both horizontal or vertical dividers. Accordingly, the container can be easily reconfigured to accept different instrument sets.

BRIEF DESCRIPTION OF THE DRAWINGS

These and other advantages of the present invention will be come apparent from the following description, with reference to the accompanying drawings, in which.

DESCRIPTION OF THE PREFERRED EMBODIMENTS

Figure 1:
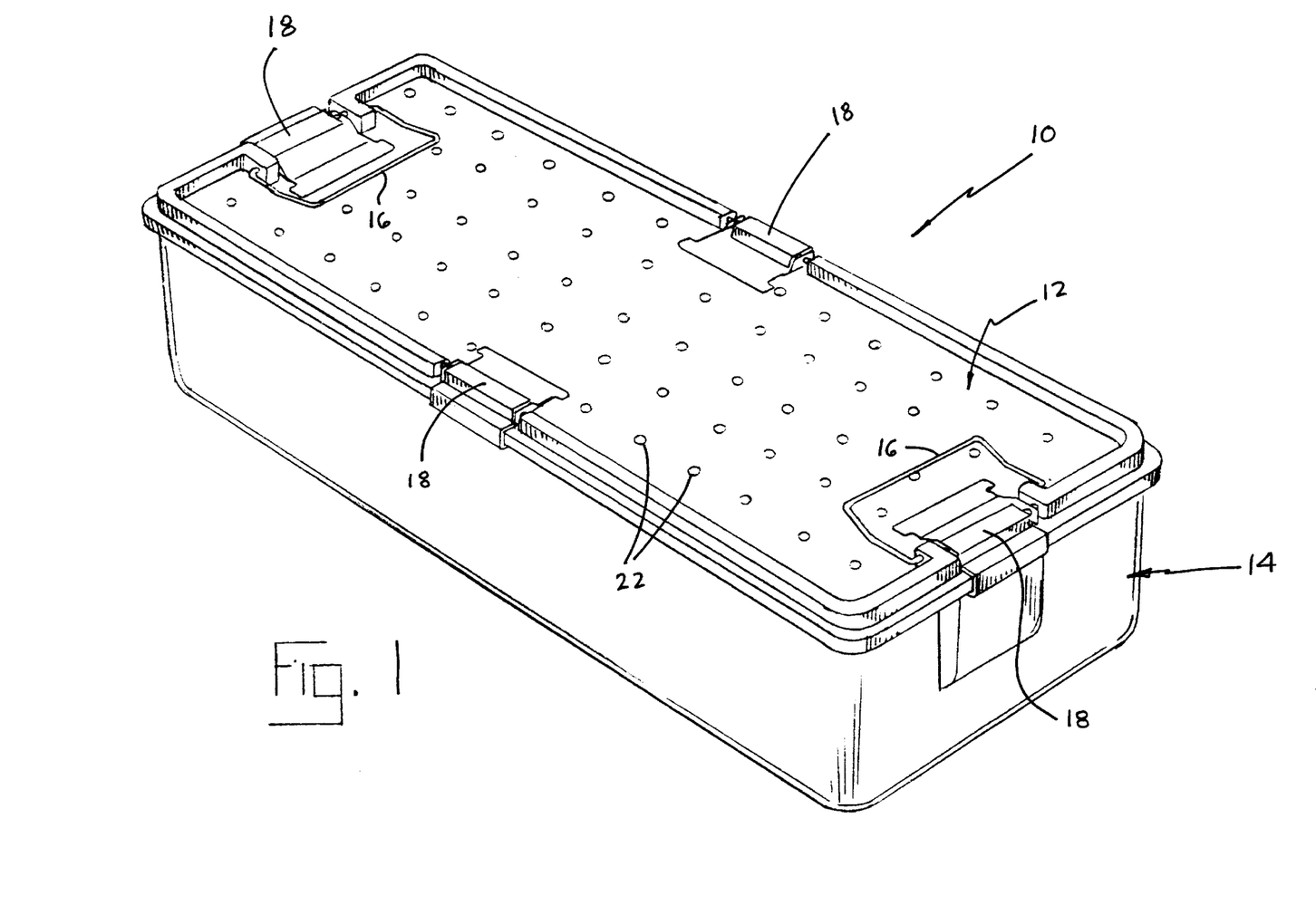
FIG. 1 is a view in perspective of a sterilization container made pursuant to the teachings of the present invention.
Figure 2:
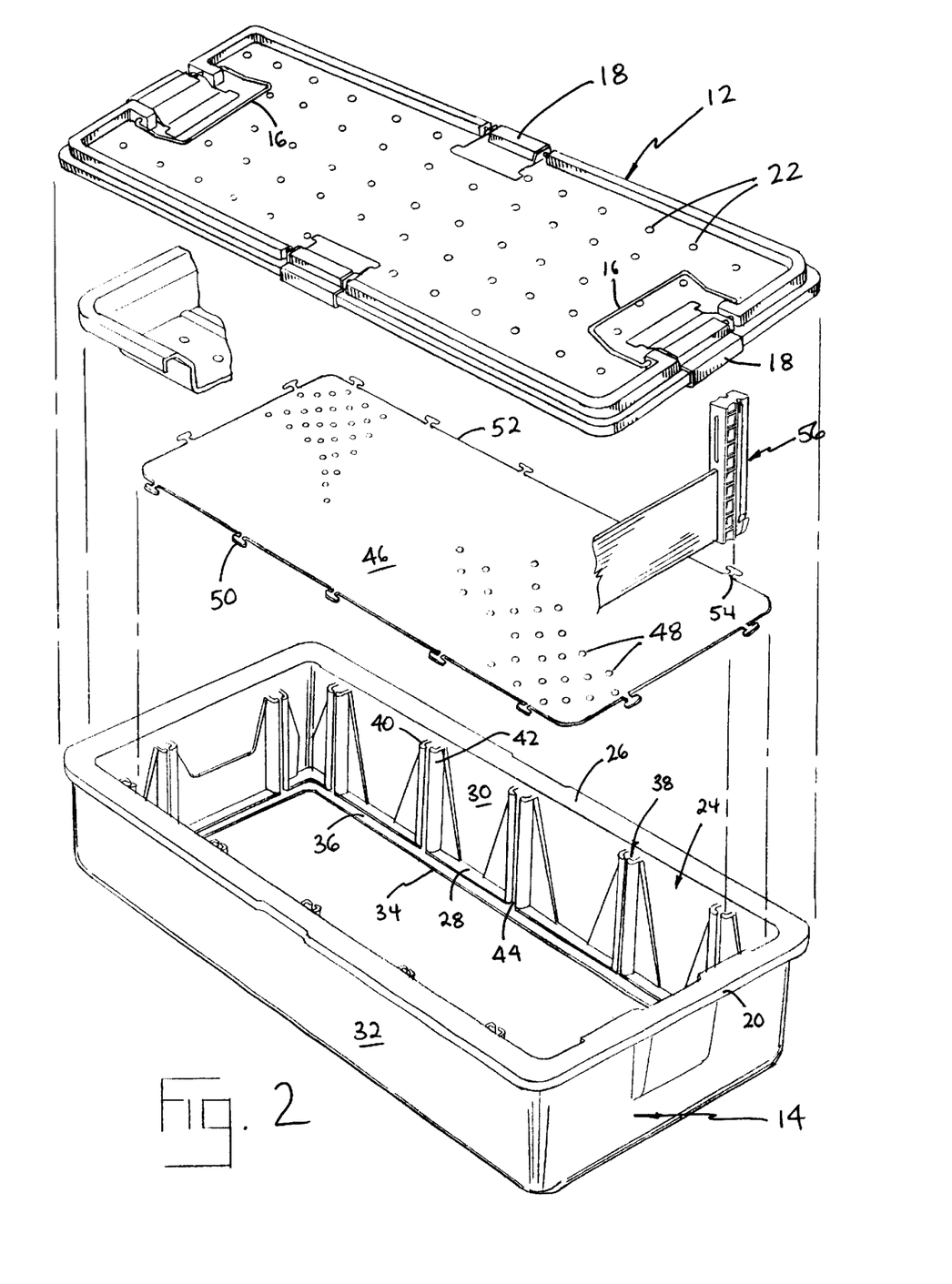
FIG. 2 is an exploded view in perspective of a sterilization container made according to the teachings of the present invention, to illustrate the internal components thereof.

Referring now to the drawings and first to FIGS. 1 and 2, a sterilization container generally indicated by the numeral 10 includes a lid 12 and a base 14. The lid 12 is provided with fold down handles 16 at opposite ends thereof and with conventional latches 18 on the edges thereof that latch against the rim 20 on the base 14. Openings 22 are provided in the lid 12 to permit circulation of sterile gasses through the container 10.

Figure 17:
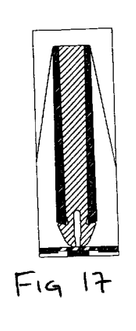
FIG. 17 is a view taken substantially along lines 17—17 of FIG. 14.
Figure 18:
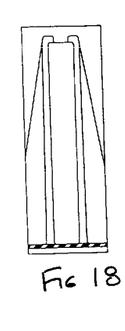
FIG. 18 is a view taken substantially along lines 18—18 of FIG. 14.

The base 14 includes a circumferentially extending wall 24 having an upper edge 26, a lower edge 28, an inner side wall surface 30, and an outer surface 32. Lower edge 28 defines a bottom opening 34, and a circumferentially extending flange 36 projects from the edge 28 into the opening 34 and circumscribes the opening 34. Circumferentially spaced channels 38 are defined between arms 40, 42 which project outwardly from the wall surface 30 and define a gap 44 therebetween. Preferably, both the lid 12 and base 14 are made of a plastic material. A bottom, preferably made of metal is indicated by the numeral 46. Bottom 46 includes openings 48 which permit sterilization gasses to pass into the container. Commonly, the bottom 46 will be customized as will be hereinafter described by the placement of appropriate separators, etc., to receive surgical instruments. It is an important feature of the invention that the bottom 46 may be replaced in the base 14 by a differently configured bottom, thus permitting the base 14 to accommodate and be upgraded to accommodate various sets of surgical instruments. Bottom 46 includes T-shaped tabs 50 that are spaced along the outer edge 52 thereof. Each of the tabs 50 is connected to the edge 52 by a necked portion 54. The bottom 46 is installed in the base 14 by installing the bottom 46 past the upper edge 26 with the tabs 50 sliding down the channels 38, with the necks 54 of the tabs 50 extending through the gaps 44. The bottom 46 is designed to rest upon, and be supported by the flange 36. Accordingly, when the bottom 46 is installed in the base 14, it is constrained against movement in every direction except vertically upwardly toward the upper edge 26. As illustrated in FIG. 17, the arms 40, 42 terminate a short distance above the flange 36.

The bottom 46 is held in place by inserts generally indicated by the numeral 56, which are received in each of the channels 38 around the wall 30. As depicted in FIGS. 3–6, the inserts 56 include a body portion 58 which is slidably received in the corresponding channel 38, a necked portion 60, which extends through the gap 44, and an outwardly projecting portion 62, which projects from the arms 40, 42. The body portion 58 includes a pair of barbs 64 at its lower end thereof as is discussed above, the inserts 56 are preferably made of a flexible, resilient silicone rubber. Accordingly, the barbs 64 deflect inwardly when the insert is installed in its corresponding channel 38, to thereby permit the body 56 to slide downwardly viewing the Figures, until the barbs 64 extend past the lower ends of the arms 40, 42, whereupon the barbs 64 deflect outwardly, thereby locking the inserts 56 in place. The length of the barbs are such that they engage the upper surface of the bottom 46, thereby yieldably resisting upward movement of the bottom. A small gap 66 is provided to permit deflection of the barb 64 as the insert 56 is installed in one of the channels 38.

Figure 10:
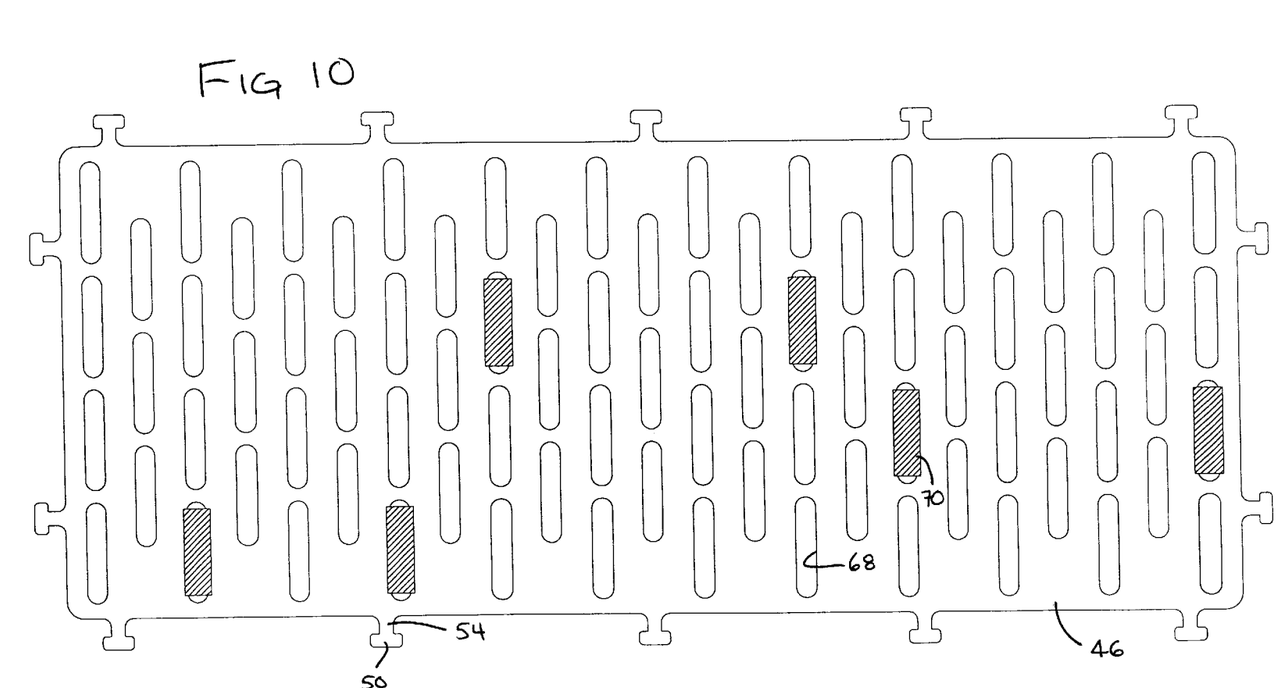
FIG. 10 is a top plan view of the bottom used in the sterilization container illustrated in FIGS. 1–2.
Figure 11:
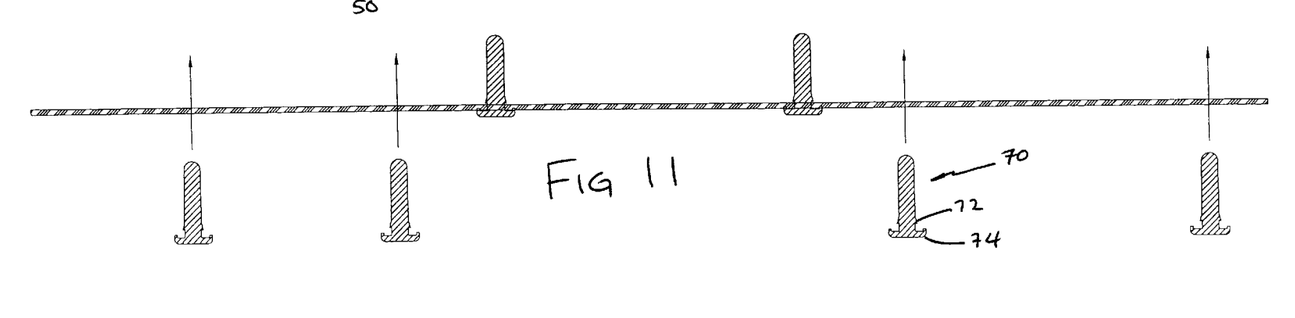
FIG. 11 is a side elevational view of the bottom illustrated in FIG. 10, illustrating the manner in which holders are placed in the base.
Figure 12:
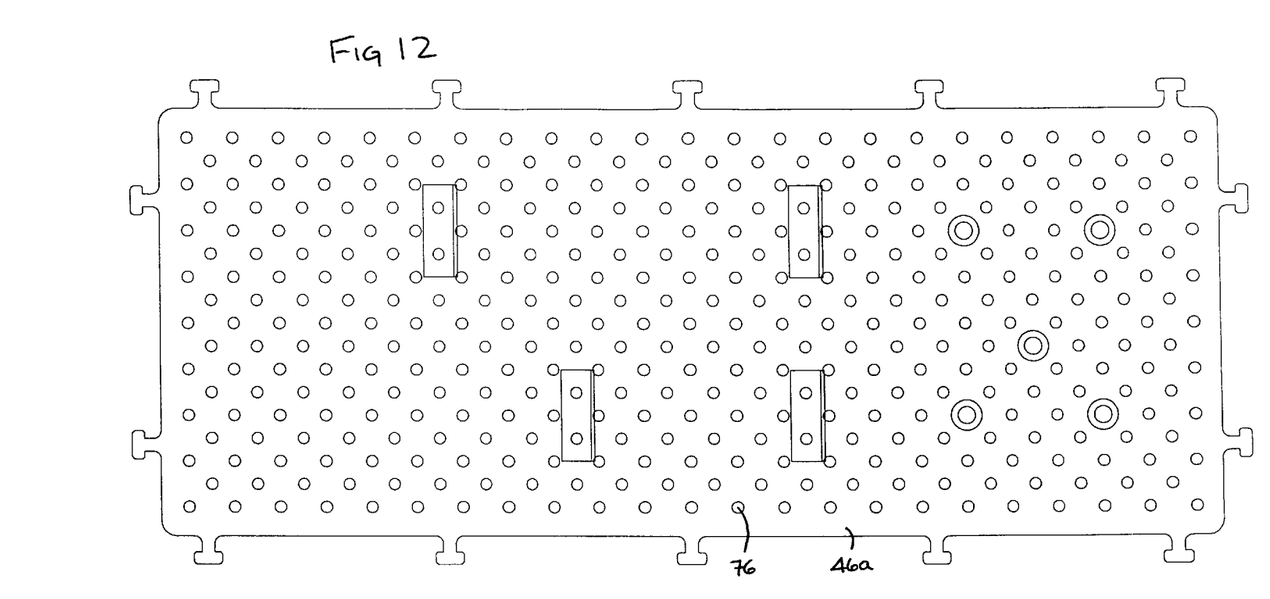
FIG. 12 is a view similar to FIG. 10, but illustrating another embodiment for the bottom.
Figure 13:
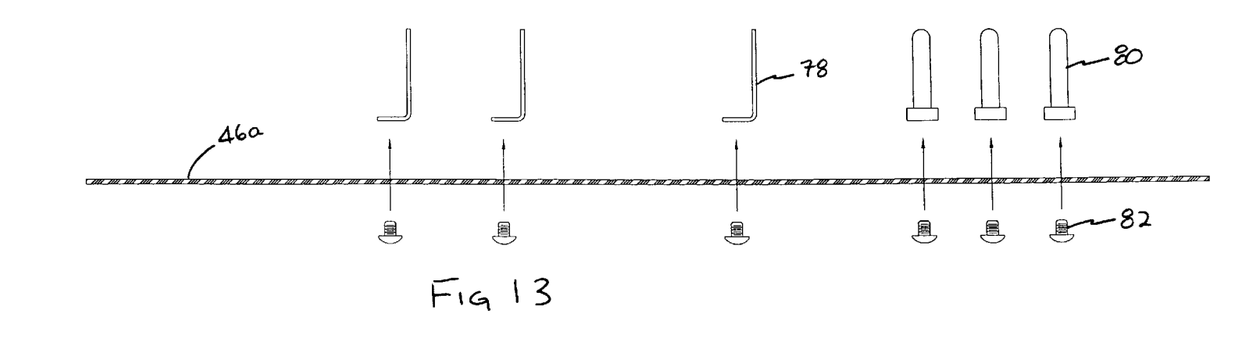
FIG. 13 is a view similar to FIG. 11, but showing the bottom illustrated in FIG. 12, and also illustrating the manner in which instrument dividers are installed on the base.
Figure 14:
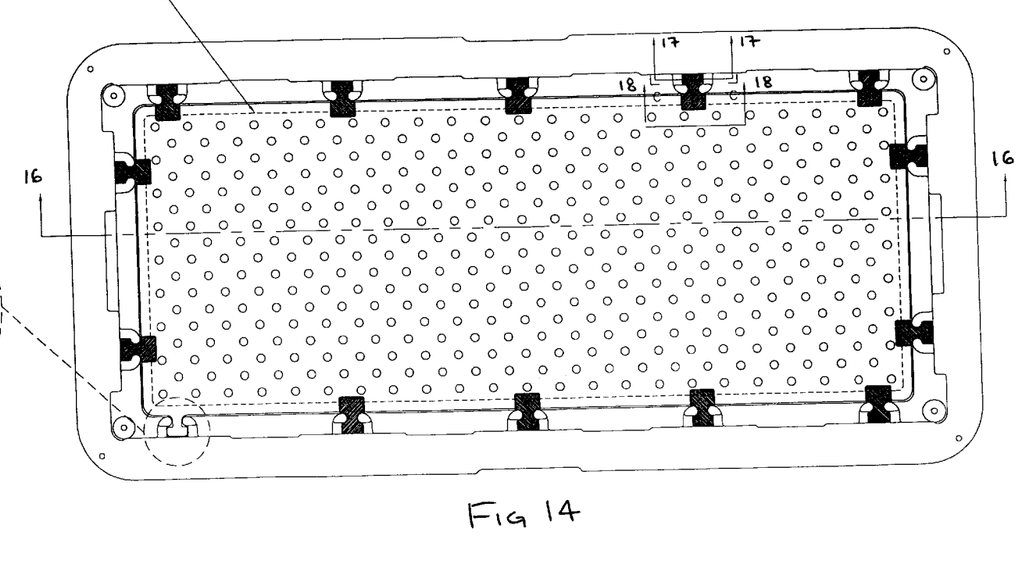
FIG. 14 is a top plan view of the sterilization container illustrated in FIGS. 1 and 2 with the bottom and inserts installed in the base.
Figure 15:
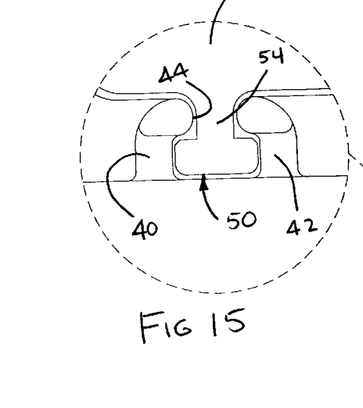
FIG. 15 is an enlarged view of the circumscribed portion of FIG. 14.

Referring to FIGS. 10 and 11, the bottom 46 is provided with elongated openings 68 which allow sterilization gasses to enter the sterilization container 10. Silicone brackets 70 are installed in selected ones of the slots 68 and are provided with barbs 72 and arms 74 which engage opposite sides of the bottom 46 to retain the brackets 70 in place. Commonly, each different instrument package requires a different number and location of the brackets 70 to properly position instruments within the container 10. Referring now to FIG. 12, the bottom 46a is provided with holes 76, also for permitting sterile gasses access to the container. Brackets 78 and posts 80 are installed on the bottom 46a by screws 82. In the case of either the bottom 46 or the bottom 46a, an important feature of the invention is that the silicone inserts 56 are removable from the channels 38, by depressing the barb 64 and then grasping the outwardly extending portion 62 and sliding the insert along the channel. Accordingly, the same base 14 may be used with reconfigured bottoms 46 to accommodate different orientations of the locating brackets and posts 70, 78, 80 without replacing the entire sterilization container 10.

Figure 16:
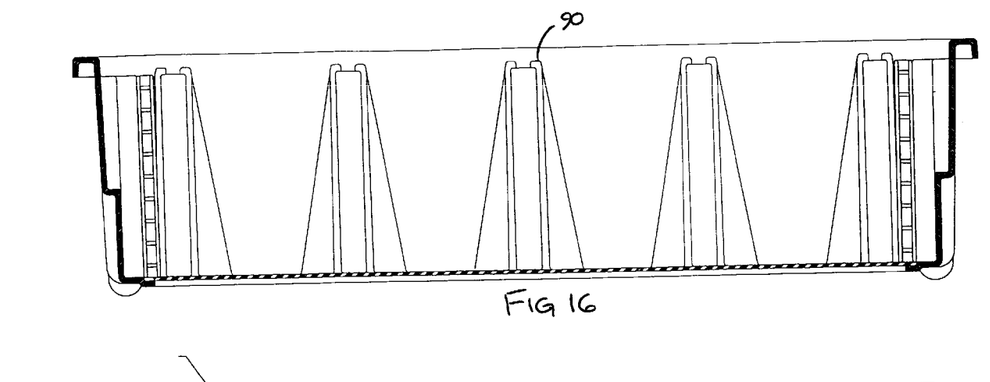
FIG. 16 is a cross sectional view taken substantially along lines 16—16 of FIG. 14.
Figure 19:
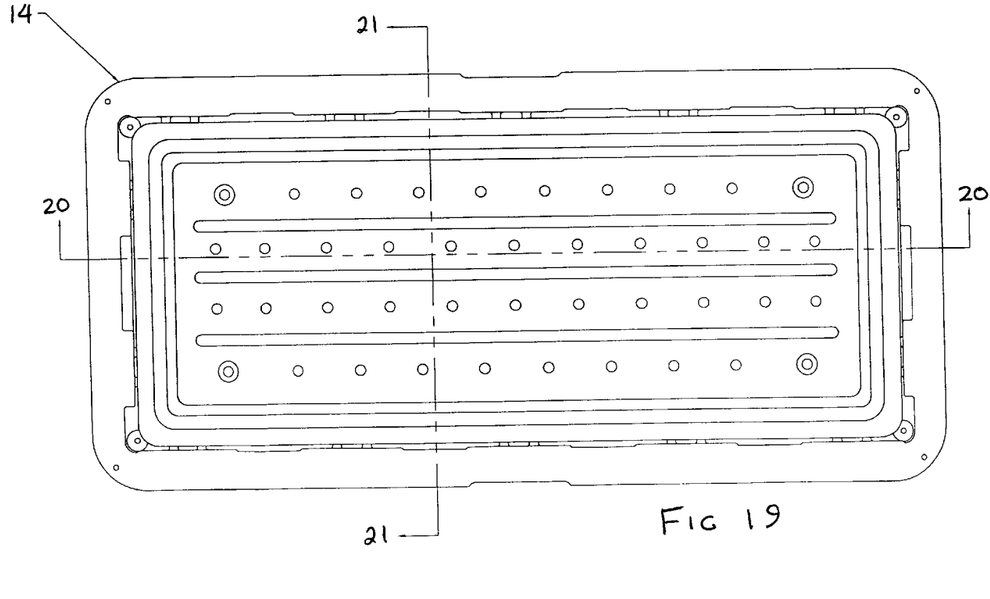
FIG. 19 is a top plan view of the sterilization container illustrated in FIGS. 1 and 2 with insert trays installed therein.
Figure 20:
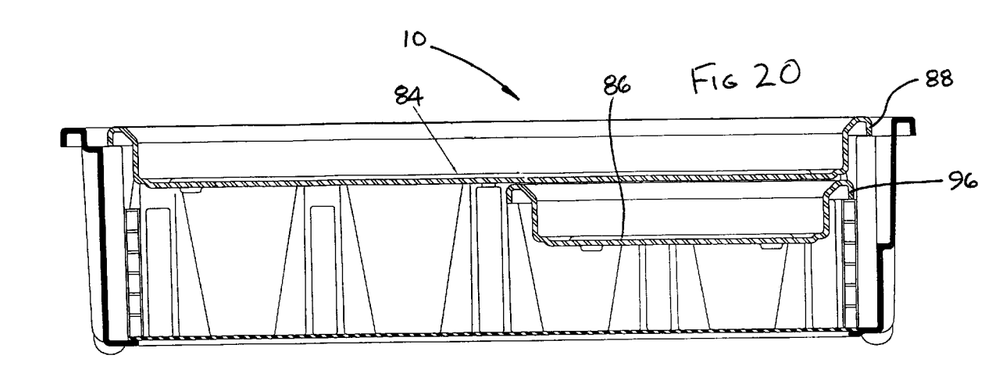
FIG. 20 is a view taken substantially along lines 20—20 of FIG. 19.
Figure 21:
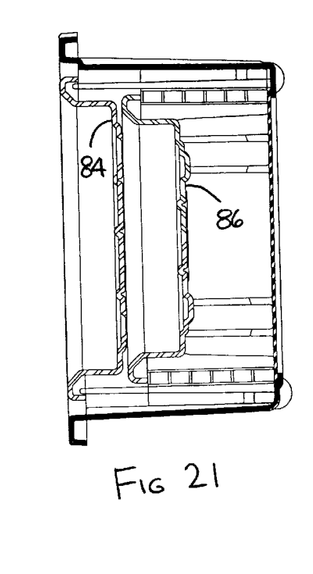
FIG. 21 is a view taken substantially along lines 21—21 of FIG. 19.

Instrument sets commonly require one or more insert trays. These insert trays vary greatly, depending upon the instrument set, in size and vertical location within the container 10. Referring to FIGS. 19–21, the sterilization container 10 is configured with an upper insert tray 84, which extends completely across the length and width of the sterilization container 10, and a lower insert tray 86, which extends completely across the width of the container, but extends less than the full length of the container. Depending upon the instrument set, the tray 86 may be located at any one of several vertical heights within the container 10. The tray 84 is provided with a circumferentially extending supporting flange 88 that, when the tray 84 is installed in the container, rests upon the upper edges 90 (FIG. 16) of the arms 40, 42 defining the channels 38, and/or the upper surfaces 92 (FIGS. 4 and 5) of body portion 58 of the inserts 56. These upper surfaces 90, 92 define a landing supporting the flange 88 to thereby support the tray 84 within the container 10. The trays 84, 86 are made of a plastic material, and are provided with openings 94 to allow the sterilization gasses to pass through the trays.

Figure 5:
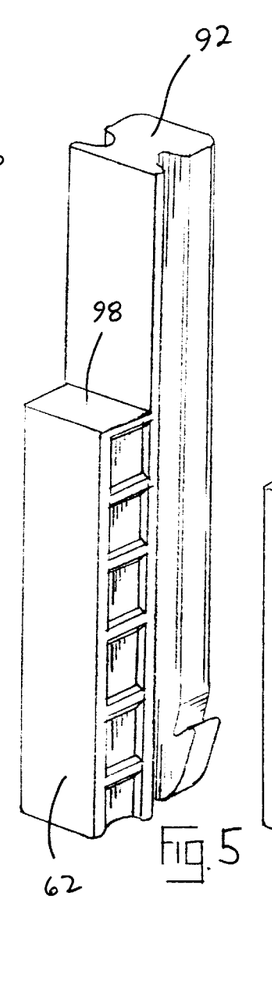
Figure 6:
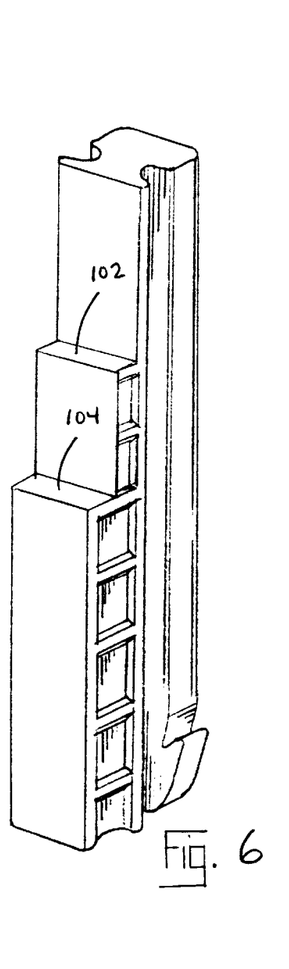
Figure 7:
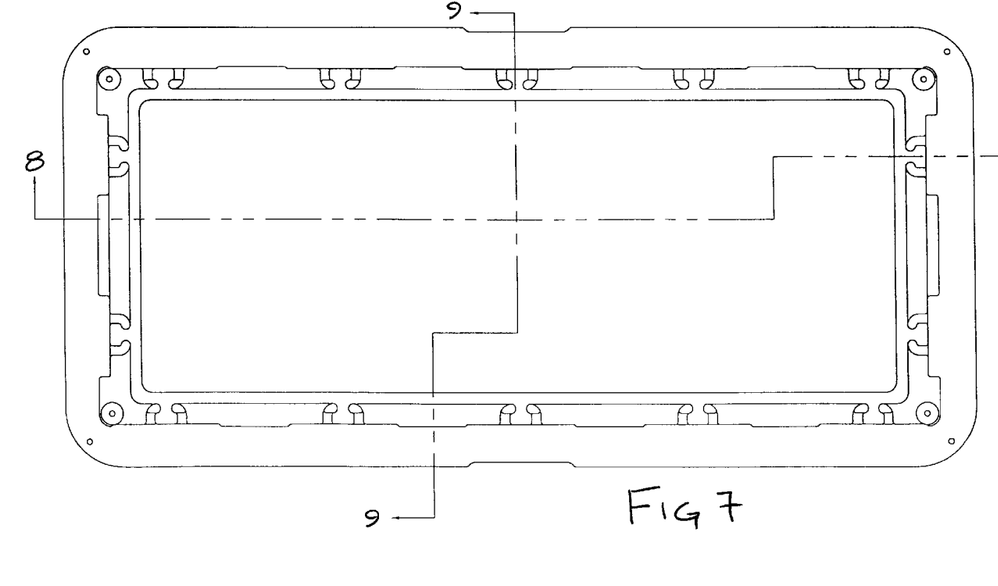
FIG. 7 is a top plan view of the base of the sterilization container illustrated in FIGS. 1–2.
Figure 8:
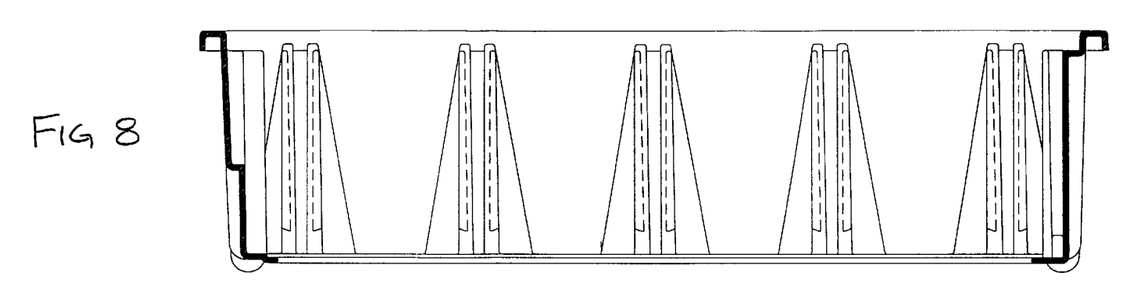
FIG. 8 is a cross sectional view taken substantially along lines 8—8 of FIG. 7.
Figure 9:
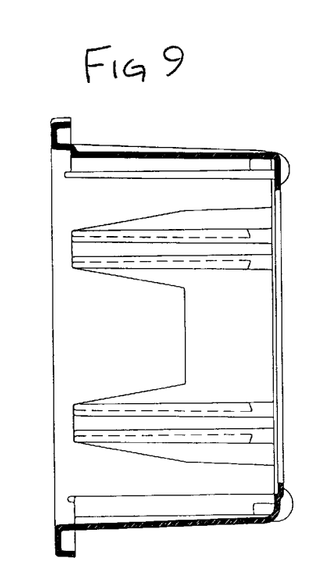
FIG. 9 is a cross sectional view taken substantially along lines 9—9 of FIG. 7.

The lower insert tray 86 is provided with a circumferentially extending flange 96 (FIG. 20) which is supported by the inserts 56a (FIG. 5). The inserts 56a is trimmed from an original insert 56 to include landings 98 on the outwardly extending portions 62 of the inserts installed in channels which the flange 96 traverses. The landings 98 are formed by manually trimming a section of the outwardly extending portion 62 of the corresponding inserts 56 away to form the landing 98. Measurement markings 100 are provided on the outwardly extending portions of the inserts 56 to facilitate trimming of the landings 98. Accordingly, the inserts 56 may be trimmed at any necessary level to provide landings to support one or more insert trays 86 at the required height. Referring to FIG. 6, an insert 56b is formed where the outwardly extending portion 62 may be trimmed to define steps, thereby defining an upper landing 102 and a lower landing 104 to support vertically offset insert trays. The container 10 may be reconfigured to accommodate different sets of instruments by removing the corresponding inserts and replacing them with trimmed inserts with the outwardly extending portion 62 trimmed at the appropriate level.

Figure 22:
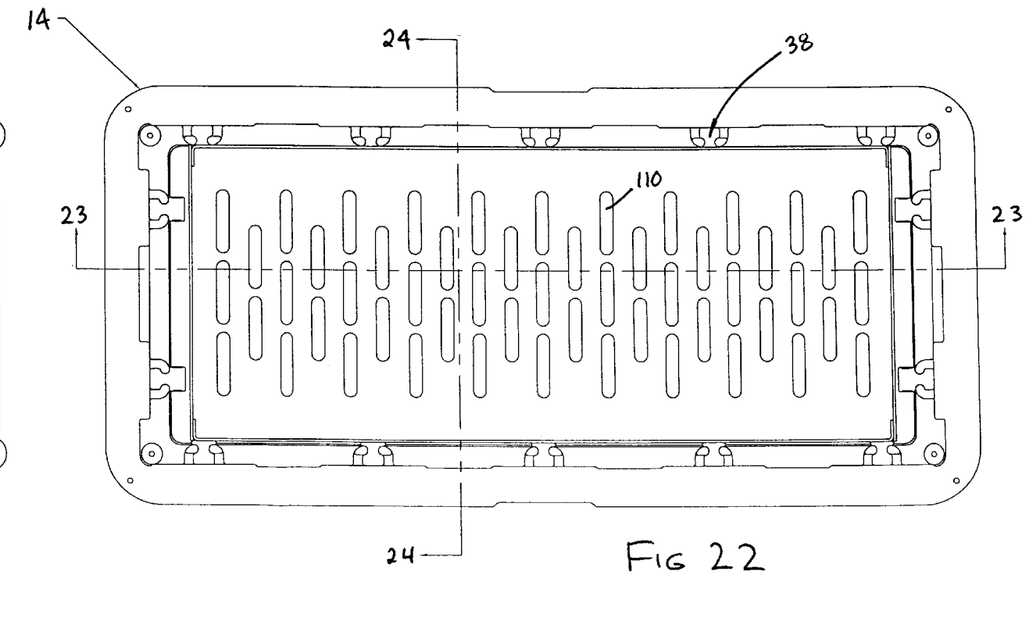
FIG. 22 is a view similar to FIG. 19, but illustrating metal insert trays received within the sterilization container.
Figure 23:
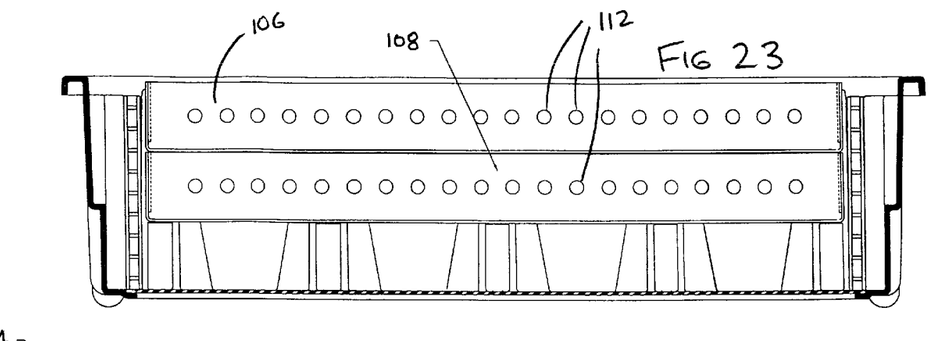
FIG. 23 is a cross sectional view taken substantially along lines 23—23 of FIG. 22.
Figure 24:
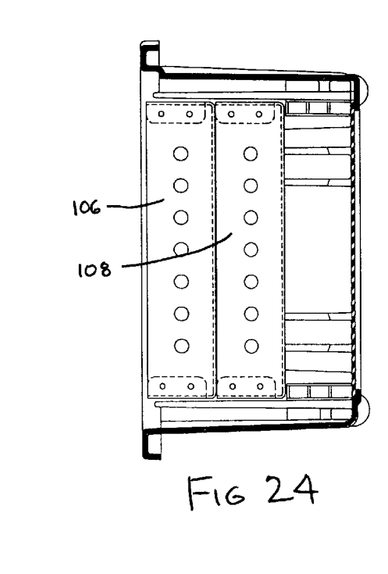
FIG. 24 is a cross sectional view taken substantially along lines 24—24 of FIG. 22.

Referring now to FIGS. 22–24, the sterilization container 10 may also accommodate metal insert trays 106, 108. The metal insert trays 106, 108 are substantially identical with one another, and extend across the width of the container between the arms defining the channels 38 on opposite sides of the container. The insert trays 106, 108 are of a length less than the length of the container. The lower tray 108 is supported on landings 98 trimmed in the outwardly extending portion 62 of the inserts 56 located on the opposite sides of the container. Since the tray 108 has a length less than the length of the container, the inserts on the end channels on the ends of the container are not trimmed. The tray 106 is designed to rest upon the tray 108, in manner well known to those skilled in the art. The trays 106, 108 are provided with slots 110 in the bottoms thereof and holes 112 in the sides thereof to permit circulation of the sterilization gasses.

Figures 3, 4:
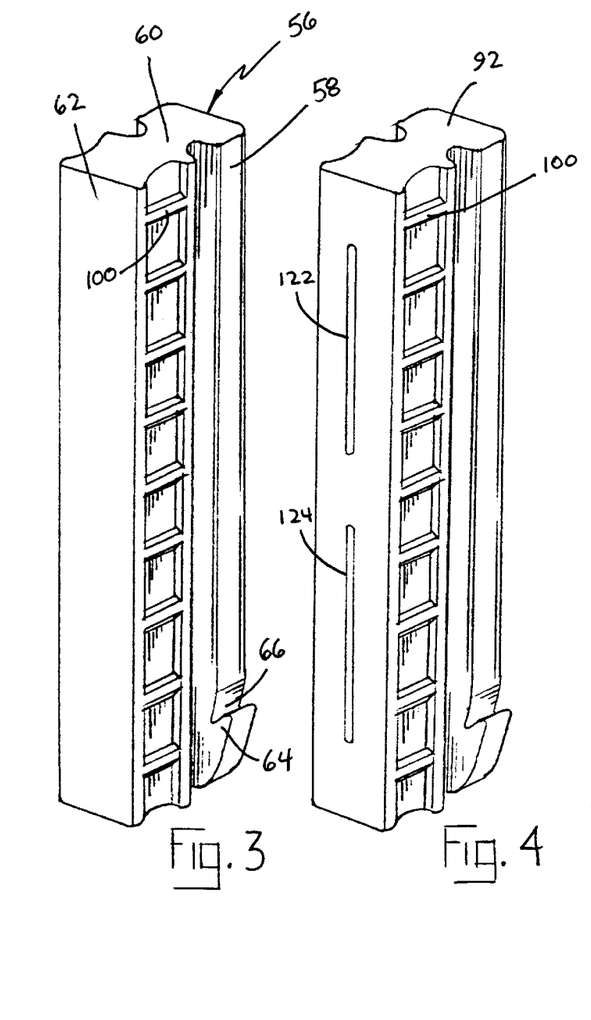
FIGS. 3–6 are views in perspective of various inserts used to both secure the bottom on the base of the sterilization container of the present invention and also to provide landings to support insert trays.
Figures 25, 26, 27, 28:
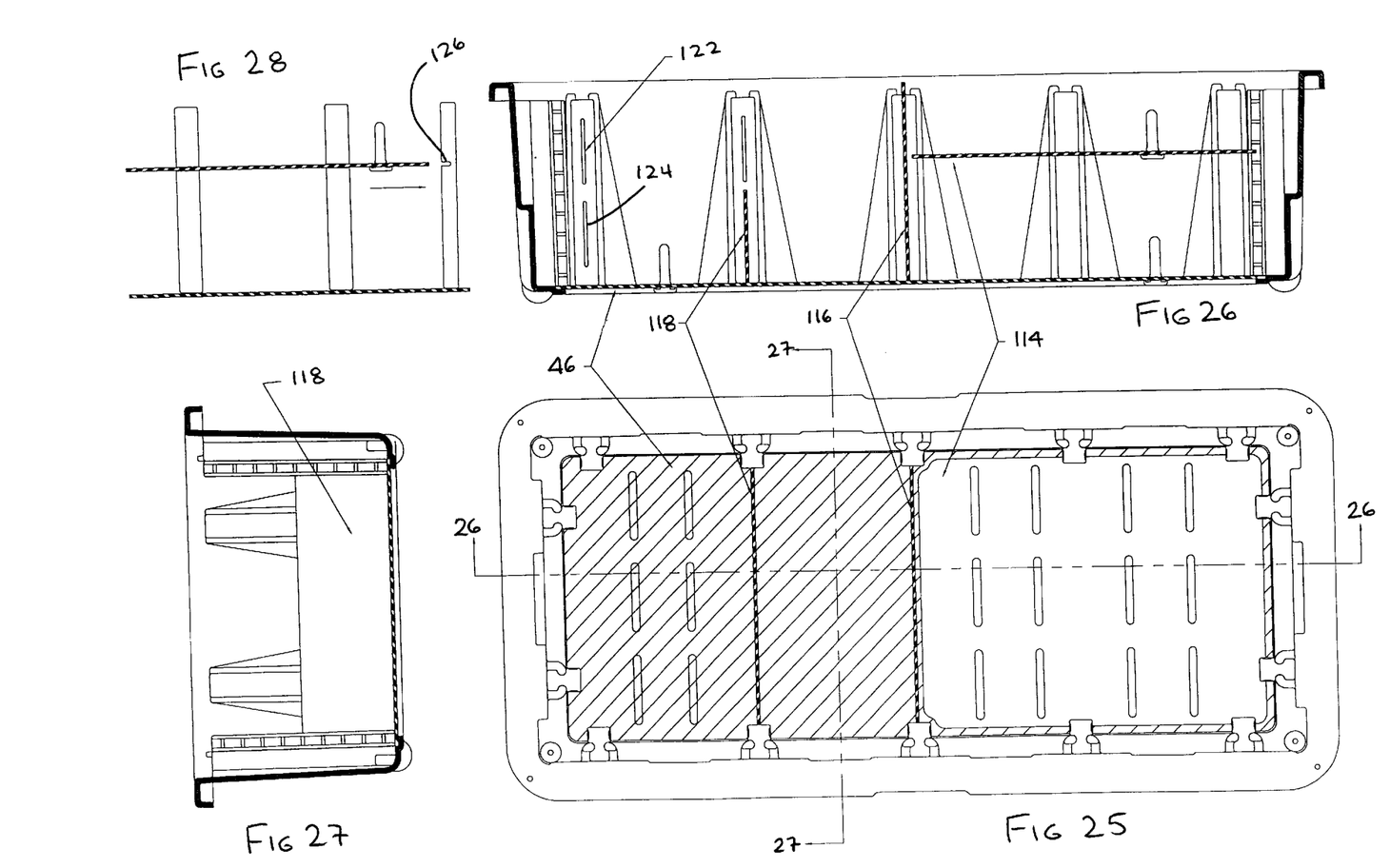
FIG. 25 is a top plan view of the sterilization container illustrated in FIGS. 1 and 2, but illustrating vertical and horizontal dividers installed therein.
FIG. 26 is a cross sectional view taken substantially along lines 26—26 of FIG. 25.
FIG. 27 is a cross sectional view taken substantially along lines 27—27 of FIG. 25.
FIG. 28 is a diagrammatic illustration illustrating the manner in which the horizontal dividers are installed in the inserts held by the base.
Figure 29:
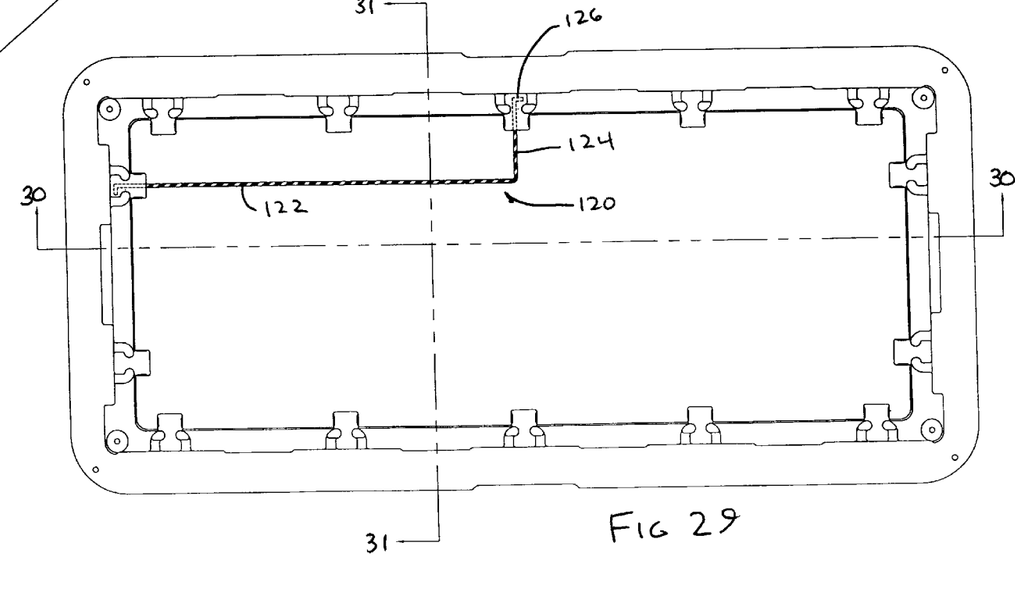
FIG. 29 is a view similar to FIG. 25, but illustrating a different type of vertical divider installed in the sterilization container.
Figure 30:
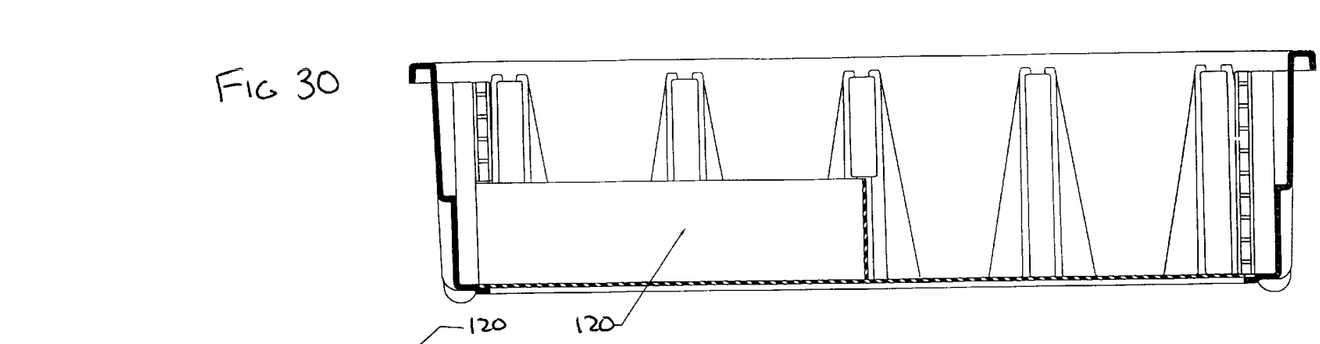
FIG. 30 is a cross sectional view taken substantially along lines 30—30 of FIG. 29.
Figure 31:
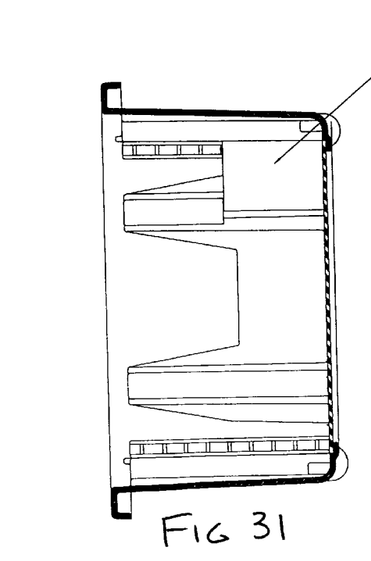
FIG. 31 is a view taken substantially along lines 31—31 of FIG. 30.

Referring now to FIGS. 25–31, some instrument sets require dividers which divide the volume within the container 10 into sections. Such dividers include horizontal dividers 114, which may be placed at any height depending upon the instrument set, and extend over a section of the container. Vertical dividers include both full height vertical dividers 116, or dividers 118 of less than full height. Referring to FIG. 4, the outwardly extending portion 62 of the inserts 56 may be provided with vertically extending upper and lower slots 122, 124. Slots 122, 124 on the inserts directly across from one another receive tabs extending from the opposite edges of the full height divider 116, whereas the partial height of divider 118 includes tabs that are received only in the lower slots 124. In either case, the dividers are securely positioned within the sterilization container 10. As shown in FIG. 28, the outwardly extending portions of the inserts 56 may also be provided with horizontally extending slots 126, to accept the edge of the horizontal divider 114, to thereby secure the horizontal divider at its proper vertical location. The outwardly extending portion 62 may be notched manually at the correct height to accept the horizontal divider 114. Referring to FIGS. 29–31, the interior volume of the container 10 may also be compartmentalized by dividers that have both longitudinal and transverse components, such as the divider indicated at 120. As shown in FIGS. 29–31, divider 120 includes both longitudinally extending portion 122 and transversely extending portion 124. Both of these portions include tabs 126 on the ends thereof that are received within the slots 124, as described above, of the corresponding inserts located respectively on the end wall and one of the side walls of the container 10. As is the case with the trays 84, 86 and 108 and 110, the inserts may be removed, reconfigured, and reinstalled to accommodate dividers 114, 116, 118, and 120 of different types and in different locations, to thereby permit the container 10 to be adapted for different instrument sets.

A modified insert 130 is shown in FIGS. 32–35, and includes a body portion 132 which fits within channel 38, a necked portion 134 which is retained between arms 40–42 of the base 14, and an outwardly projecting portion 136. Extending along the longitudinal dimension of outwardly projecting portion 136 of each insert 130 are a series of nibs or markings 138 which are equally spaced apart.

Figures 32, 33, 34, 35:
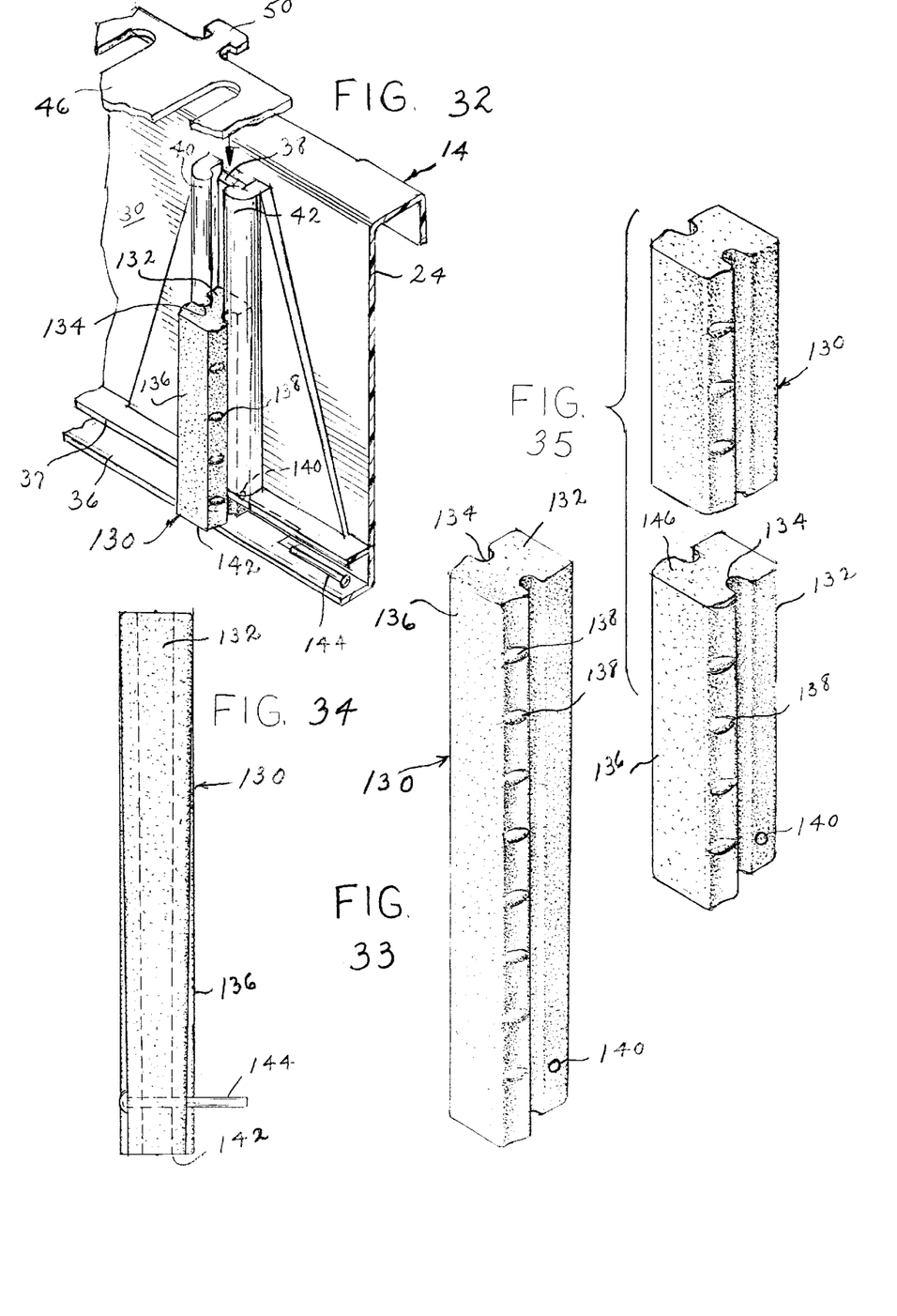
FIG. 32 is a fragmentary perspective view of a modified insert in use.
FIG. 33 is a perspective view of the modified insert.
FIG. 34 is a rear view of the modified insert showing the retainer pin inserted.
FIG. 35 is a view of the modified insert shown in separated form.

A bore 140 extends transversely through body part 132 of each insert 130. With the insert fitted into channel 38 as illustrated in FIG. 32 and having its lower end face 142 resting upon flange 36, bore 140 will be located just below the adjacent and parallel upper flange 37 of base 14. A pin 144 is inserted through bore 140 and each insert 130, protruding beyond the transverse dimension of body part 132 just under flange 37 so as to provide a stop which prevents the insert from being withdrawn upwardly relative to base 14 within its receiving channel 38. Thus, if one attempts to remove an insert 130 from its receiving channel 38, pin 144 which is positioned and extends through bore 140 of the insert will contact flange 37 preventing removal.

As illustrated in FIG. 35, each insert 130 which may be of a flexible, resilient silicone rubber may be severed or cut along a selected marking 138 so as to provide a platform 146 at a selected height above flange 36 of base 14. Also each insert 130 may include slots 122, 124 whose purpose was earlier described. Bottom 46 as described earlier, can be inserted with its tabs 50 each fitting within a receiving slot and lowered until it rests upon landings 146 of the inserts 130. In this manner, the height of bottom 46 can be selectively varied within base 14.

The invention is not to be limited to the details above given but may be modified within the scope of the appended claims.

The preferred embodiments illustrated are not intended to limit the invention to the precise forms enclosed. They are chosen and described to best illustrate the invention and to enable a person having an ordinary skill in the art to utilize the invention.

What is claimed is:

1. Sterilization container for sterilizing and storing medical instruments comprising a base having a circumferentially extending wall defining a volume for receiving medical instruments, said wall having an inner surface, an outer surface, an upper edge defining a top opening, a bottom edge defining a bottom opening, and a circumferentially extending flange projecting inwardly into said bottom opening from said bottom edge, a perforated bottom closing said bottom opening supported by said flange, and a plurality of retainers mounted on said inner surface for restraining movement of the bottom toward said flange, and a lid closing said top opening, said retainers include circumferentially spaced, axially extending channels on said inner surface, and an insert each of said channels, each of said inserts being slidable within its corresponding channels, said inserts being latched against upward movement relative to said channel when the inserts are moved into a latched position restraining movement of said inserts toward said upper edge, said channels have a lower edge, said inserts including outwardly projecting deflectable barbs engaging the lower ends of the channels to restrain movement of the insert toward said upper edge to thereby lock the corresponding insert in said latched position.

2. Sterilization container as claimed in claim 1, wherein at least some of said inserts include outwardly projecting portions projecting outwardly from said channels into said volume, at least some of said projecting portions defining a landing extending substantially parallel to the top and bottom edges for engaging support edges of removable trays placed in said volume whereby the landings support the trays off of said bottom.

3. Sterilization container as claimed in claim 2, Therein the inserts have an upper end adjacent the upper edge of the base and the landing is defined on the outwardly projecting portions of at least some of said inserts is offset vertically from the upper end of the inserts.

4. Sterilization container as claimed in claim 2, wherein the outwardly projecting portions of at least some of said inserts are stepped vertically to define higher and lower landings for engaging support edges of removable trays placed in said volume to support said trays one below the other.

5. Sterilization container as claimed in claim 2, wherein the projecting portions of the inserts are made of a material that is sufficiently soft to permit the projecting portion to be modified by manually trimming the insert at a selected vertical level to define a landing at the selected vertical level.

6. Sterilization container as claimed in claim 1, wherein said channels are defined by a pair of arms projecting into said volume to define said channels therebetween, said arms terminating in contiguous ends defining a gap therebetween, said inserts including a body portion within the channel, a neck extending through said gap, and a projecting portion extending from said neck into said volume.

7. Sterilization container as claimed in claim 2, wherein said projecting portion terminates at a landing offset from the end of the body portion to define a landing supporting said removable tray at a level below the end of the body portion.

8. Sterilization container as claimed in claim 2, wherein at least some of said projecting portions are provided with slots extending axially with respect to said base when the inserts are installed in their corresponding channels, said slots receiving a portion of an axially extending divider wall extending between two of said channels to divide said volume into sections.

9. Sterilization container as claimed in claim 2, wherein at least some of said projecting portions includes a slot extending parallel to the top and bottom edges of the base when the inserts are installed in the channels, said slots receiving an edge portion of a divider plate extending parallel to said bottom.

10. Sterilization container for sterilizing and storing medical instruments comprising a base having a circumferentially extending wall defining a volume for receiving medical instruments, said wall having an inner surface, an outer surface, an upper edge defining a top opening, a bottom edge defining a bottom opening, and a circumferentially extending flange projecting inwardly into said bottom opening from said bottom edge, a perforated bottom closing said bottom opening supported by said flange, and a plurality of retainers mounted on said inner surface for restraining movement of the bottom toward said flange, and a lid closing said top opening, said retainers include circumferentially spaced, axially extending channels on said inner surface, and an insert for each of said channels, each of said inserts being slidable within its corresponding channels, said inserts being latched against upward movement relative to said channel when the inserts are moved into a latched position restraining movement of said inserts toward said upper edge, said bottom includes edges having outwardly projecting tabs, said tabs being received in said channels when the bottom is installed in said base.

11. Sterilization container for sterilizing and storing medical instruments comprising a base having a perforated bottom and a circumferentially extending wall defining a volume for receiving medical instruments, said wall having an inner surface, an outer surface, an upper edge defining a top opening, circumferentially spaced, axially extending channels on said inner surface, and an insert for each of said channels, at least some of said inserts include outwardly projecting portions projecting outwardly from said channels into said volume, at least some of said projecting portions defining a landing extending substantially parallel to the top and bottom edges for engaging support edges of removable trays placed in said volume whereby the landings support the trays off of said bottom.

12. Sterilization container as claimed in claim 11, wherein the inserts have an upper end adjacent the upper edge of the base and the landing is defined on the outwardly projecting portions of at least some of said inserts is offset vertically from the upper end of the inserts.

13. Sterilization container as claimed in claim 11, wherein the outwardly projecting portions of at least some of said inserts are stepped vertically to define higher and lower landings for engaging support edges of removable trays placed in said volume to support said trays one below the other.

14. Sterilization container as claimed in claim 11, wherein the projecting portions of the inserts include selected markings for severing the projecting portion at a selected vertical level to define a landing at the selected vertical level.

15. Sterilization container as claimed in claim 11, wherein longitudinally offset measuring marks are provided on the projecting portions of the inserts to permit the projecting portions to be modified to provide a landing a predetermined level.

16. Sterilization container as claimed in claim 11, wherein said channels are defined by a pair of arms projecting into said volume to define said channels therebetween, said arms terminating in contiguous ends defining a gap therebetween, said inserts including a body portion within the channel, a neck extending through said gap, and a projecting portion extending from said neck into said volume.

17. Sterilization container as claimed in claim 16, wherein said projecting portion terminates at a landing offset from the end of the body portion to define a landing supporting removable tray at a level below the end of the body portion.

18. Sterilization container as claimed in claim 11, wherein at least some of said projecting portions are provided with slots extending axially with respect to said base when the inserts are installed in their corresponding channels, said slots receiving a portion of an axially extending divider wall extending between two of said channels to divide said volume into section.

19. Sterilization container as claimed in claim 11, wherein at least some of said projecting portions includes a slot extending parallel to the top and bottom edges of the base when the inserts are installed in the channels, said slots receiving an edge portion of a divider plate extending parallel to said bottom.

20. Sterilization container as claimed in claim 1, wherein said wall includes a second circumferentially extending flange projecting inwardly into said bottom opening and spaced above said first mentioned wall flange, said channels having a lower edge at said second flange, said inserts extending within said channels and through said second flange, pins extending through said inserts and having projecting portions underlying said second flange to restrain said inserts from being removed upwardly from said channels.

* * * * *

UNITED STATES PATENT AND TRADEMARK OFFICE
CERTIFICATE OF CORRECTION

PATENT NO. : 6,585,942 B1
DATED : July 1, 2003
INVENTOR(S) : Bussell et al.

It is certified that error appears in the above-identified patent and that said Letters Patent is hereby corrected as shown below:

Column 6,
Line 47, delete the word "Therein" and insert -- wherein --

Column 8,
Line 18, insert the word -- at -- between "landing" and "a"

Signed and Sealed this

Twelfth Day of August, 2003

JAMES E. ROGAN
*Director of the United States Patent and Trademark Office*